United States Patent
Vaillancourt

(10) Patent No.: US 9,713,673 B2
(45) Date of Patent: *Jul. 25, 2017

(54) HUBER NEEDLE WITH SAFETY SHEATH

(71) Applicant: Bard Access Systems, Inc., Salt Lake City, UT (US)

(72) Inventor: Michael J. Vaillancourt, Chester, NJ (US)

(73) Assignee: Bard Access Systems, Inc., Salt Lake City, UT (US)

( * ) Notice: Subject to any disclaimer, the term of this patent is extended or adjusted under 35 U.S.C. 154(b) by 228 days.

This patent is subject to a terminal disclaimer.

(21) Appl. No.: 14/045,663

(22) Filed: Oct. 3, 2013

(65) Prior Publication Data

US 2014/0039416 A1 Feb. 6, 2014

Related U.S. Application Data

(63) Continuation of application No. 11/788,542, filed on Apr. 20, 2007, now Pat. No. 8,597,253.

(51) Int. Cl.
*A61M 5/158* (2006.01)
*A61M 5/32* (2006.01)

(52) U.S. Cl.
CPC .......... *A61M 5/158* (2013.01); *A61M 5/3257* (2013.01); *A61M 2005/1581* (2013.01); *A61M 2005/325* (2013.01); *A61M 2005/3258* (2013.01)

(58) Field of Classification Search
CPC .......... A61M 5/158; A61M 2005/1581; A61M 5/3243
See application file for complete search history.

(56) References Cited

U.S. PATENT DOCUMENTS

| 2,847,995 | A | 8/1958 | Adams |
| 2,876,770 | A | 3/1959 | White |
| 2,925,083 | A | 2/1960 | Craig |
| 3,134,380 | A | 5/1964 | Armao |
| 3,306,290 | A | 2/1967 | Weltman |
| 4,160,450 | A | 7/1979 | Doherty |

(Continued)

FOREIGN PATENT DOCUMENTS

| DE | 3808688 A1 | 1/1989 |
| DE | 3802353 A1 | 8/1989 |

(Continued)

OTHER PUBLICATIONS

EP 03257490 filed Nov. 27, 2003 Office Action dated Aug. 9, 2007.

(Continued)

*Primary Examiner* — Bradley Osinski
(74) *Attorney, Agent, or Firm* — Rutan & Tucker, LLP

(57) ABSTRACT

A safety needle assembly is described, including a cap, a housing movable relative to the cap from a first position adjacent the cap to an extended second position spaced from the cap, a hollow needle secured in and extending from the housing, and a collapsible sheath secured to both the cap and the housing. The sheath is concentrically disposed about the needle in a collapsed state with the housing in the first position. The sheath is extendable from the collapsed state to an extended state in response to movement of the housing from the first position to the second position.

8 Claims, 3 Drawing Sheets

(56) References Cited

U.S. PATENT DOCUMENTS

| | | | |
|---|---|---|---|
| 4,235,234 A | 11/1980 | Whitney et al. | |
| 4,352,254 A | 10/1982 | Peter et al. | |
| 4,352,354 A | 10/1982 | Ujihara et al. | |
| 4,380,234 A | 4/1983 | Kamen | |
| 4,435,175 A | 3/1984 | Friden | |
| 4,464,178 A * | 8/1984 | Dalton | A61M 39/0208 128/DIG. 26 |
| 4,564,054 A | 1/1986 | Gustavsson | |
| 4,592,744 A | 6/1986 | Jagger et al. | |
| 4,611,382 A | 9/1986 | Clark | |
| 4,615,468 A | 10/1986 | Gay | |
| 4,627,842 A | 12/1986 | Katz | |
| 4,627,843 A | 12/1986 | Raines | |
| 4,631,058 A | 12/1986 | Raines | |
| 4,632,671 A | 12/1986 | Dalton | |
| 4,645,494 A | 2/1987 | Lee et al. | |
| 4,645,495 A | 2/1987 | Vaillancourt | |
| 4,655,765 A | 4/1987 | Swift | |
| 4,676,782 A | 6/1987 | Yamamoto et al. | |
| 4,676,783 A | 6/1987 | Jagger et al. | |
| 4,676,788 A | 6/1987 | Vincent | |
| 4,695,274 A | 9/1987 | Fox | |
| 4,710,176 A | 12/1987 | Quick | |
| 4,725,267 A | 2/1988 | Vaillancourt | |
| 4,755,173 A | 7/1988 | Konopka et al. | |
| 4,760,847 A | 8/1988 | Vaillancourt | |
| 4,775,369 A | 10/1988 | Schwartz | |
| 4,813,939 A | 3/1989 | Marcus | |
| 4,820,282 A | 4/1989 | Hogan | |
| D301,742 S | 6/1989 | Wyzgala et al. | |
| 4,846,809 A | 7/1989 | Sims | |
| 4,867,172 A | 9/1989 | Haber et al. | |
| 4,897,083 A * | 1/1990 | Martell | 604/192 |
| 4,935,011 A | 6/1990 | Hogan | |
| 4,935,013 A | 6/1990 | Haber et al. | |
| 4,941,881 A | 7/1990 | Masters et al. | |
| 4,941,882 A | 7/1990 | Ward et al. | |
| 4,944,731 A | 7/1990 | Cole | |
| 4,950,250 A | 8/1990 | Haber et al. | |
| 4,969,876 A | 11/1990 | Patterson | |
| 5,013,305 A | 5/1991 | Opie et al. | |
| 5,053,017 A | 10/1991 | Chamuel | |
| 5,061,250 A | 10/1991 | Shields | |
| 5,085,639 A | 2/1992 | Ryan | |
| 5,088,982 A | 2/1992 | Ryan | |
| 5,092,852 A | 3/1992 | Poling | |
| 5,120,320 A | 6/1992 | Fayngold | |
| 5,176,653 A | 1/1993 | Metals | |
| 5,176,655 A | 1/1993 | McCormick et al. | |
| 5,176,662 A | 1/1993 | Bartholomew et al. | |
| 5,192,275 A | 3/1993 | Burns | |
| 5,197,954 A | 3/1993 | Cameron | |
| 5,236,421 A | 8/1993 | Becher | |
| 5,295,972 A | 3/1994 | Mischenko | |
| 5,312,366 A | 5/1994 | Vailancourt | |
| 5,312,371 A | 5/1994 | Dombrowski et al. | |
| 5,330,438 A | 7/1994 | Gollobin et al. | |
| 5,334,158 A | 8/1994 | McLees | |
| 5,336,187 A | 8/1994 | Terry et al. | |
| 5,336,199 A * | 8/1994 | Castillo et al. | 604/198 |
| 5,342,319 A | 8/1994 | Watson et al. | |
| 5,342,320 A | 8/1994 | Cameron | |
| 5,350,368 A | 9/1994 | Shields | |
| 5,354,281 A | 10/1994 | Chen et al. | |
| 5,419,766 A | 5/1995 | Chang et al. | |
| 5,433,703 A | 7/1995 | Utterberg et al. | |
| 5,451,522 A | 9/1995 | Queener et al. | |
| 5,487,728 A | 1/1996 | Vaillancourt | |
| 5,487,733 A | 1/1996 | Caizza et al. | |
| 5,490,841 A | 2/1996 | Landis | |
| 5,505,711 A | 4/1996 | Arakawa et al. | |
| 5,520,654 A | 5/1996 | Wahlberg | |
| 5,531,704 A | 7/1996 | Knotek | |
| 5,531,713 A | 7/1996 | Mastronardi et al. | |
| 5,554,106 A | 9/1996 | Layman-Spillar et al. | |
| 5,567,495 A | 10/1996 | Modak et al. | |
| 5,569,207 A | 10/1996 | Gisselberg et al. | |
| 5,575,773 A | 11/1996 | Song et al. | |
| 5,584,813 A | 12/1996 | Livingston et al. | |
| 5,584,818 A | 12/1996 | Morrison | |
| 5,607,398 A | 3/1997 | Parmigiani | |
| 5,620,424 A | 4/1997 | Abramson | |
| 5,637,096 A | 6/1997 | Yoon | |
| 5,662,913 A | 9/1997 | Capelli | |
| 5,674,201 A | 10/1997 | Steinman | |
| 5,685,860 A | 11/1997 | Chang et al. | |
| 5,686,096 A | 11/1997 | Khan et al. | |
| 5,693,022 A | 12/1997 | Haynes | |
| 5,695,474 A | 12/1997 | Daugherty | |
| 5,706,520 A | 1/1998 | Thornton et al. | |
| 5,722,959 A | 3/1998 | Bierman | |
| 5,755,694 A | 5/1998 | Camus et al. | |
| 5,762,632 A | 6/1998 | Whisson | |
| 5,779,679 A | 7/1998 | Shaw | |
| 5,817,070 A | 10/1998 | Tamaro | |
| 5,833,665 A | 11/1998 | Bootman et al. | |
| 5,848,990 A * | 12/1998 | Cirelli et al. | 604/136 |
| 5,853,393 A | 12/1998 | Bogert | |
| 5,858,004 A | 1/1999 | Shields | |
| 5,879,330 A | 3/1999 | Bell | |
| 5,885,254 A | 3/1999 | Matyas | |
| 5,885,255 A | 3/1999 | Jaeger, Jr. et al. | |
| 5,951,522 A | 9/1999 | Rosato et al. | |
| 5,951,525 A | 9/1999 | Thorne et al. | |
| 5,993,426 A | 11/1999 | Hollister | |
| 6,042,570 A | 3/2000 | Bell et al. | |
| 6,165,156 A | 12/2000 | Cesarczyk et al. | |
| 6,238,375 B1 | 5/2001 | Powell | |
| 6,451,003 B1 | 9/2002 | Prosl et al. | |
| 6,497,669 B1 | 12/2002 | Kensey | |
| 6,497,682 B1 | 12/2002 | Quartararo | |
| 6,500,155 B2 | 12/2002 | Sasso | |
| 6,537,255 B1 | 3/2003 | Raines | |
| 6,579,539 B2 | 6/2003 | Lawson et al. | |
| 6,613,015 B2 | 9/2003 | Sandstrom et al. | |
| 6,623,462 B2 | 9/2003 | Guzzo et al. | |
| 6,629,959 B2 | 10/2003 | Kuracina et al. | |
| 6,659,984 B2 | 12/2003 | Maclean Crawford et al. | |
| 6,663,604 B1 | 12/2003 | Huet | |
| 6,676,633 B2 | 1/2004 | Smith et al. | |
| 6,689,102 B2 | 2/2004 | Greene | |
| 6,699,217 B2 | 3/2004 | Bennett et al. | |
| 6,719,727 B2 | 4/2004 | Brimhall et al. | |
| 6,749,588 B1 | 6/2004 | Howell et al. | |
| 6,755,805 B1 | 6/2004 | Reid | |
| 6,783,002 B1 | 8/2004 | Pavlo | |
| 6,808,509 B1 | 10/2004 | Davey | |
| 6,824,530 B2 | 11/2004 | Wagner et al. | |
| 6,911,020 B2 | 6/2005 | Raines | |
| 6,916,310 B2 | 7/2005 | Sommerich | |
| 6,918,894 B2 | 7/2005 | Fleury et al. | |
| 6,921,388 B2 | 7/2005 | Swenson | |
| 6,926,693 B2 | 8/2005 | Enns | |
| 6,932,803 B2 | 8/2005 | Newby | |
| 6,969,372 B1 | 11/2005 | Halseth | |
| 6,972,002 B2 | 12/2005 | Thorne | |
| 6,997,902 B2 * | 2/2006 | Thorne et al. | 604/110 |
| 7,147,623 B2 | 12/2006 | Mathiasen | |
| 7,150,725 B2 | 12/2006 | Wilkinson | |
| 7,214,208 B2 | 5/2007 | Vaillancourt et al. | |
| 7,361,159 B2 | 4/2008 | Fiser et al. | |
| 7,407,493 B2 | 8/2008 | Cane' | |
| 7,438,703 B2 | 10/2008 | Barrus et al. | |
| 7,569,044 B2 | 8/2009 | Triplett et al. | |
| 7,601,139 B2 | 10/2009 | Woehr et al. | |
| 7,604,616 B2 | 10/2009 | Thoresen et al. | |
| 7,637,893 B2 | 12/2009 | Christensen et al. | |
| 7,662,159 B2 | 2/2010 | Brandigi | |
| 7,717,888 B2 | 5/2010 | Vaillancourt et al. | |
| 7,776,016 B1 | 8/2010 | Halseth et al. | |
| 7,947,021 B2 | 5/2011 | Bourne et al. | |
| 7,967,797 B2 | 6/2011 | Winsor et al. | |
| 8,066,678 B2 | 11/2011 | Vaillancourt et al. | |
| 8,152,768 B2 | 4/2012 | Halseth et al. | |

(56) References Cited

U.S. PATENT DOCUMENTS

| | | |
|---|---|---|
| 8,263,100 B2 | 9/2012 | Areskoug et al. |
| 8,293,965 B2 | 10/2012 | McMaken et al. |
| 8,486,004 B1 | 7/2013 | Propp |
| 8,569,567 B2 | 10/2013 | Ovington |
| 8,574,197 B2 | 11/2013 | Halseth et al. |
| 8,579,863 B2 | 11/2013 | Scherr |
| 8,597,253 B2 | 12/2013 | Vaillancourt |
| 8,728,029 B2 | 5/2014 | Vaillancourt et al. |
| 8,852,154 B2 | 10/2014 | Halseth et al. |
| 2001/0039401 A1 | 11/2001 | Ferguson et al. |
| 2002/0055711 A1 | 5/2002 | Lavi et al. |
| 2002/0072716 A1 | 6/2002 | Barrus et al. |
| 2002/0099340 A1 | 7/2002 | Crawford et al. |
| 2002/0151852 A1 | 10/2002 | Crawford et al. |
| 2002/0165497 A1 | 11/2002 | Greene |
| 2002/0173749 A1 | 11/2002 | Wagner et al. |
| 2002/0177816 A1 | 11/2002 | Brimhall et al. |
| 2002/0177818 A1 | 11/2002 | Vaillancourt |
| 2002/0183652 A1 | 12/2002 | Kensey |
| 2003/0060774 A1 | 3/2003 | Woehr et al. |
| 2003/0069546 A1 | 4/2003 | Sandstrom et al. |
| 2003/0093101 A1 | 5/2003 | O'Heeron et al. |
| 2003/0105430 A1 | 6/2003 | Lavi et al. |
| 2003/0114797 A1* | 6/2003 | Vaillancourt ....... A61M 5/3213 604/171 |
| 2003/0144627 A1 | 7/2003 | Woehr et al. |
| 2003/0148994 A1 | 8/2003 | Levinson |
| 2003/0181872 A1 | 9/2003 | Newby |
| 2003/0199827 A1 | 10/2003 | Thorne |
| 2004/0044318 A1 | 3/2004 | Fiser et al. |
| 2004/0049159 A1 | 3/2004 | Barrus et al. |
| 2004/0156908 A1 | 8/2004 | Polaschegg |
| 2004/0236288 A1 | 11/2004 | Howell et al. |
| 2005/0027263 A1 | 2/2005 | Woehr et al. |
| 2005/0090784 A1 | 4/2005 | Nielsen et al. |
| 2005/0107743 A1 | 5/2005 | Fangrow |
| 2005/0107748 A1 | 5/2005 | Thorne et al. |
| 2005/0107749 A1 | 5/2005 | Smith et al. |
| 2005/0124938 A1 | 6/2005 | Yang |
| 2005/0137528 A1 | 6/2005 | Wilkinson |
| 2005/0191355 A1* | 9/2005 | Foss ....................... A01N 57/16 424/486 |
| 2006/0064061 A1 | 3/2006 | Solomon et al. |
| 2006/0074387 A1 | 4/2006 | Thorne et al. |
| 2006/0155245 A1 | 7/2006 | Woehr |
| 2006/0161116 A1 | 7/2006 | Willis et al. |
| 2006/0253076 A1 | 11/2006 | Butts et al. |
| 2006/0276836 A1 | 12/2006 | Bergin et al. |
| 2007/0038182 A1 | 2/2007 | Bialecki et al. |
| 2007/0038183 A1 | 2/2007 | Bialecki et al. |
| 2007/0038184 A1 | 2/2007 | Bialecki et al. |
| 2007/0038185 A1 | 2/2007 | Albert et al. |
| 2007/0073221 A1 | 3/2007 | Bialecki et al. |
| 2007/0073222 A1 | 3/2007 | Lilley et al. |
| 2007/0078432 A1 | 4/2007 | Halseth et al. |
| 2008/0063693 A1 | 3/2008 | Cook et al. |
| 2008/0147003 A1 | 6/2008 | Menzi et al. |
| 2008/0243082 A1 | 10/2008 | Goodman |
| 2008/0262434 A1 | 10/2008 | Vaillancourt |
| 2009/0005743 A1 | 1/2009 | Vaillancourt et al. |
| 2009/0143737 A1 | 6/2009 | Kobayashi et al. |
| 2009/0157000 A1 | 6/2009 | Waller |
| 2009/0254050 A1 | 10/2009 | Bottcher |
| 2009/0281499 A1 | 11/2009 | Harding et al. |
| 2010/0076362 A1 | 3/2010 | Utterberg et al. |
| 2010/0100049 A1 | 4/2010 | Godfrey |
| 2010/0179473 A1 | 7/2010 | Genosar |
| 2010/0312183 A1 | 12/2010 | Halseth et al. |
| 2011/0021997 A1 | 1/2011 | Kyvik et al. |
| 2011/0106014 A1 | 5/2011 | Helm, Jr. |
| 2011/0111012 A1 | 5/2011 | Pepper et al. |
| 2011/0301619 A1 | 12/2011 | Walters |
| 2012/0046612 A1 | 2/2012 | Scheremet et al. |
| 2012/0046621 A1 | 2/2012 | Vaillancourt et al. |
| 2012/0065587 A1 | 3/2012 | Barron et al. |
| 2012/0089069 A1 | 4/2012 | Patel |
| 2012/0130315 A1 | 5/2012 | Weadock et al. |
| 2012/0184922 A1 | 7/2012 | Halseth et al. |
| 2013/0110025 A1 | 5/2013 | Donnellan et al. |
| 2013/0150791 A1 | 6/2013 | Peterson et al. |
| 2013/0150796 A1 | 6/2013 | Souza et al. |
| 2013/0172260 A1 | 7/2013 | Polaschegg |
| 2013/0190724 A1 | 7/2013 | Polaschegg |
| 2014/0058354 A1 | 2/2014 | Halseth et al. |
| 2014/0066894 A1 | 3/2014 | Pearce et al. |
| 2015/0297867 A1 | 10/2015 | Howell et al. |

FOREIGN PATENT DOCUMENTS

| | | |
|---|---|---|
| DE | 20210394 U1 | 9/2002 |
| EP | 0344606 A2 | 12/1989 |
| EP | 451040 A1 | 10/1991 |
| EP | 0747082 A2 | 12/1996 |
| EP | 0763369 A1 | 3/1997 |
| EP | 1350537 A1 | 10/2003 |
| EP | 1430921 A2 | 6/2004 |
| EP | 2613824 A1 | 7/2013 |
| FR | 2684006 A1 | 5/1993 |
| JP | 61-25558 A | 5/1994 |
| JP | 6226919 A | 8/1994 |
| JP | H06-304254 A | 11/1994 |
| JP | 7-148270 A | 6/1995 |
| JP | 9099071 A | 4/1997 |
| JP | 2002345955 A | 12/2002 |
| JP | 2003-305128 A | 10/2003 |
| JP | 4355567 | 8/2009 |
| JP | 2010-000300 A | 1/2010 |
| WO | 8807387 A1 | 10/1988 |
| WO | 9400172 A1 | 1/1994 |
| WO | 9806642 | 2/1998 |
| WO | 9959660 A1 | 11/1999 |
| WO | 2004020033 A1 | 3/2004 |
| WO | 2005049116 A1 | 6/2005 |
| WO | 2006134100 A1 | 12/2006 |
| WO | 2007094898 A2 | 8/2007 |
| WO | 2012034085 A1 | 3/2012 |

OTHER PUBLICATIONS

EP 03257490 filed Nov. 27, 2003 Search Report dated Jul. 23, 2004.
JP 2003-416415 filed Dec. 15, 2003 Office Action dated Feb. 23, 2007.
JP 2003-416415 filed Dec. 15, 2003 Office Action dated May 30, 2006.
PCT/US11/51102 International Preliminary Report on Patentabillity dated Mar. 21, 2013.
PCT/US11/51102 International Search Report and Written Opinion dated Dec. 23, 2011.
U.S. Appl. No. 10/320,168, filed Dec. 16, 2002 Advisory Action dated Aug. 22, 2005.
U.S. Appl. No. 10/320,168, filed Dec. 16, 2002 Advisory Action dated Nov. 16, 2005.
U.S. Appl. No. 10/320,168, filed Dec. 16, 2002 Final Office Action dated Jul. 13, 2005.
U.S. Appl. No. 10/320,168, filed Dec. 16, 2002 Non-Final Office Action dated Sep. 3, 2004.
U.S. Appl. No. 10/320,168, filed Dec. 16, 2002 Notice of Allowance dated Aug. 29, 2011.
U.S. Appl. No. 10/320,168, filed Dec. 16, 2002 Notice of Allowance dated May 13, 2011.
U.S. Appl. No. 10/787,605, filed Feb. 26, 2004 Advisory Action dated Jul. 16, 2007.
U.S. Appl. No. 10/787,605, filed Feb. 26, 2004 Final Office Action dated Apr. 4, 2008.
U.S. Appl. No. 10/787,605, filed Feb. 26, 2004 Final Office Action dated Jan. 20, 2010.
U.S. Appl. No. 10/787,605, filed Feb. 26, 2004 Final Office Action dated Jan. 25, 2007.
U.S. Appl. No. 10/787,605, filed Feb. 26, 2004 Non-Final Office Action dated Jul. 28, 2006.

(56) References Cited

OTHER PUBLICATIONS

U.S. Appl. No. 10/787,605, filed Feb. 26, 2004 Non-Final Office Action dated Oct. 2, 2008.
U.S. Appl. No. 10/787,605, filed Feb. 26, 2004 Non-Final Office Action dated Sep. 10, 2007.
U.S. Appl. No. 11/788,542, filed Apr. 20, 2007 Decision on Appeal dated Oct. 24, 2012.
U.S. Appl. No. 11/788,542, filed Apr. 20, 2007 Examiner's Answer dated Jun. 3, 2010.
U.S. Appl. No. 11/788,542, filed Apr. 20, 2007 Final Office Action dated Dec. 16, 2009.
U.S. Appl. No. 11/788,542, filed Apr. 20, 2007 Non-Final Office Action dated Aug. 27, 2008.
U.S. Appl. No. 11/788,542, filed Apr. 20, 2007 Non-Final Office Action dated Jan. 8, 2009.
U.S. Appl. No. 11/788,542, filed Apr. 20, 2007 Non-Final Office Action dated Jul. 10, 2009.
U.S. Appl. No. 12/221,034, filed Jul. 30, 2008 Final Office Action dated Dec. 8, 2009.
U.S. Appl. No. 12/221,034, filed Jul. 30, 2008 Non-Final Office Action dated Jan. 30, 2009.
U.S. Appl. No. 12/221,034, filed Jul. 30, 2008 Non-Final Office Action dated Jun. 26, 2009.
U.S. Appl. No. 12/221,034, filed Jul. 30, 2008 Notice of Allowance dated Feb. 25, 2010.
U.S. Appl. No. 12/855,605, filed Aug. 12, 2010 Final Office Action dated Oct. 4, 2011.
U.S. Appl. No. 12/855,605, filed Aug. 12, 2010 Non-Final Office Action dated Apr. 27, 2011.
U.S. Appl. No. 12/855,605, filed Aug. 12, 2010 Notice of Allowance dated Dec. 12, 2011.
U.S. Appl. No. 13/285,774, filed Oct. 31, 2011 Non-Final Office Action dated Dec. 13, 2012.
U.S. Appl. No. 13/285,774, filed Oct. 31, 2011 Non-Final Office Action dated Jul. 3, 2012.
U.S. Appl. No. 13/285,774, filed Oct. 31, 2011 Non-Final Office Action dated Jun. 3, 2013.
U.S. Appl. No. 13/434,368, filed Mar. 29, 2012 Non-Final Office Action dated Mar. 20, 2013.
PCT/US2015/038853 filed Jul. 1, 2015 International Search Report and Written Opinion dated Oct. 6, 2015.
U.S. Appl. No. 13/229,573, filed Sep. 9, 2011, Notice of Allowance dated Jul. 15, 2015.
U.S. Appl. No. 14/070,246, filed Nov. 1, 2013 Final Office Action dated Oct. 21, 2015.
U.S. Appl. No. 13/229,573, filed Sep. 9, 2011 Advisory Action dated Aug. 5, 2014.
U.S. Appl. No. 13/229,573, filed Sep. 9, 2011 Final Office Action dated Jun. 20, 2014.
U.S. Appl. No. 13/229,573, filed Sep. 9, 2011 Final Office Action dated May 6, 2015.
U.S. Appl. No. 13/229,573, filed Sep. 9, 2011 Non-Final Office Action dated Nov. 27, 2013.
U.S. Appl. No. 13/229,573, filed Sep. 9, 2011 Non-Final Office Action dated Oct. 24, 2014.
U.S. Appl. No. 13/285,774, filed Oct. 31, 2011 Final Office Action dated Oct. 28, 2013.
U.S. Appl. No. 14/070,246, filed Nov. 1, 2013 Non-Final Office Action dated Apr. 8, 2015.
U.S. Appl. No. 14/070,319, filed Nov. 1, 2013 Notice of Allowance dated Jun. 23, 2014.
U.S. Appl. No. 14/070,246, filed Nov. 1, 2013 Non-Final Office Action dated Mar. 14, 2016.
JP2013-528355 filed Jan. 25, 2013, First Office Action dated Jun. 23, 2015.
JP2013-528355 filed Jan. 25, 2013, Second Office Action dated May 31, 2016.

* cited by examiner

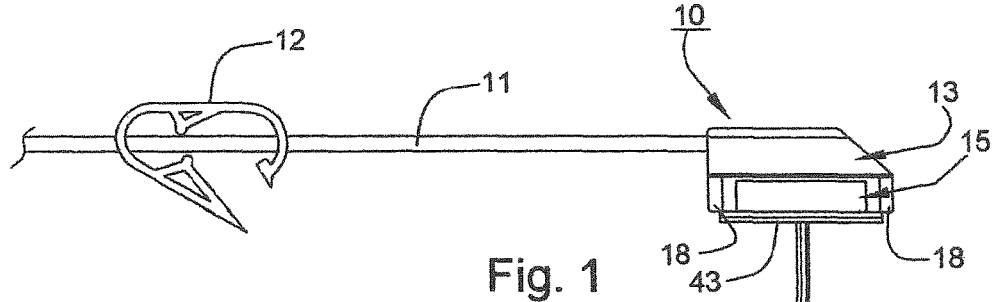
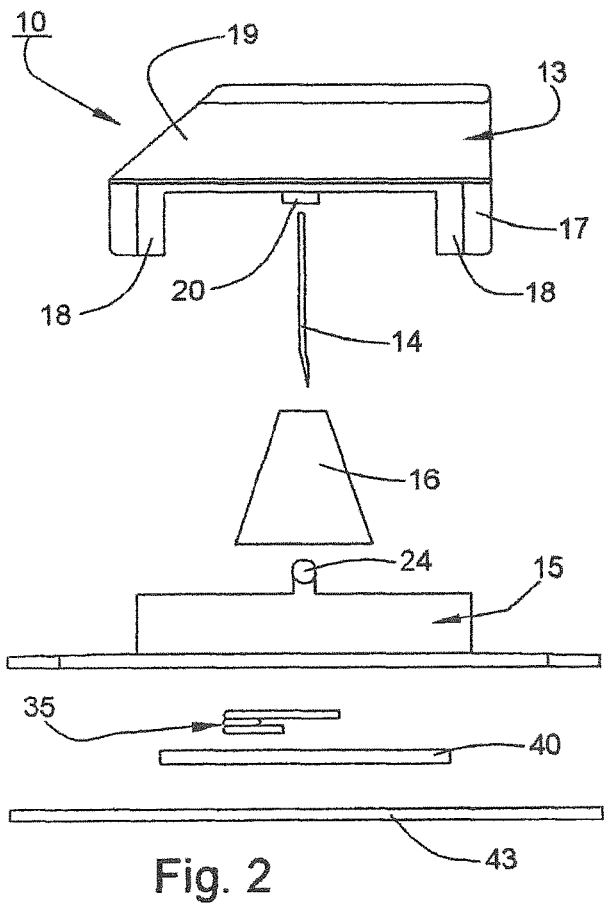
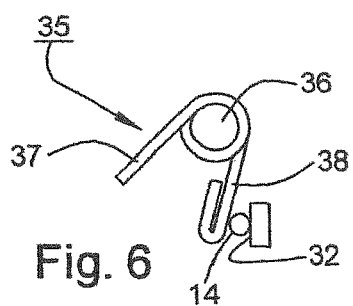
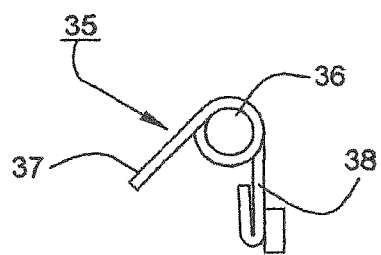

HUBER NEEDLE WITH SAFETY SHEATH

This application is a continuation of U.S. patent application Ser. No. 11/788,542, filed Apr. 20, 2007, now U.S. Pat. No. 8,597,253, which is incorporated by reference in its entirety into this application.

This invention relates to a Huber needle with a safety sheath. More particularly, this invention relates to an improved Huber needle construction.

It has been known, for example as noted in U.S. Pat. No. 4,645,494, to implant a vascular access device within the body of a patient in order to provide a convenient technique for administering drugs and fluids over a prolonged period of time. Generally, these devices include a self-sealing silicone septum encased in a port made of metal or plastic and attached to a silicone catheter. Usually, the catheter is placed in a vein of the patient for the delivery of a drug or fluid.

In order to enter the port of the vascular access device, use has been made of various types of devices and, particularly, a Huber needle. As is known, a Huber needle is bent and deflected at the distal end in order to prevent coring of a septum. Typically, the Huber needle is a right-angled needle, such as described in U.S. Pat. Nos. 6,500,155; 6,623,462; 6,824,530 and 6,969,372. When placed in use, the depending leg of the Huber needle is pierced through the skin of a patient into the port of the vascular access device implanted in the patient. In order to prevent any accidental needle stick, the exposed leg of the Huber needle has been provided with a tubular sheath that is removed prior inserting the needle into a vascular access device. However, when the Huber needle is removed from the vascular access device, the needle becomes exposed.

In order to protect against an accidental needle stick after removal of a Huber needle from a vascular access device, various techniques have been employed to sheath the exposed Huber needle. For example, U.S. Pat. No. 6,500,155 describes the use of a pair of wings that are flexed to a closed position to form an enclosed channel in which the sharpened free end of a Huber needle is to be located and confined. U.S. Pat. No. 6,623,462 describes the use of a safety guard that can be employed to remove a Huber needle assembly from a patient while encasing the exposed leg of the Huber needle. U.S. Pat. No. 6,969,372 describes the use of an automatic traction enclosure by means of which a Huber needle is retracted into a housing when being removed from use.

U.S. Pat. No. 8,066,678 describes the use of a collapsible tubular sheath and cap secured to the sheath for enclosing an exposed end of the Huber needle upon removal from a patient. As described, the cap is held against the patient while a housing in which the Huber needle is secured is moved away from the patient. During movement of the housing, the tubular sheath plays out from the housing while remaining tethered to the cap and while containing the needle therein.

In addition, the Huber needle is secured via a bushing to the interior of a line through which a liquid can be delivered to the Huber needle. However, should a high pressure be used in delivering the liquid, for example a pressure of 300 psi as can occur when delivering a fluid under emergency conditions to a patient, the delivery line can bulge radially and pull away from the outer surface of the bushing thereby creating a leakage problem.

It is an object of this invention to provide an improved Huber needle assembly.

It is another object of the invention to reduce the risk of an inadvertent "stick" from a used Huber needle.

It is another object of the invention to maintain a used Huber needle in a sealed condition for disposal.

It is another object of this invention to provide a positive locking feature for a cap to be disposed over the sharpened end of a used Huber needle.

Briefly the invention provides a safety needle assembly comprised of a housing in which a hollow needle with a bent distal end is secured in depending manner and a cap that has a bore receiving the needle and that is movable relative to the housing from a first position on the housing to an extended position spaced from the housing with the end of the needle disposed therein.

In addition, the assembly includes a sheath that is secured to and between the housing and the cap concentrically about the needle. The sheath is of frusto-conical shape and is in a collapsed state with the cap on the housing. The sheath is longitudinally extendable from the collapsed state to an extended state in response to movement of the cap away form the housing to the extended position of the cap in order to contain the needle therein.

The frusto-conical shape of the sheath allows the sheath to be collapsed into a flatter contour than a tubular sheath of equal length thereby occupying a smaller height within the assembly. In this respect, the sheath may be housed in either the housing or the cap for manufacturing purposes.

The needle assembly also has a means in the cap for closing over the bore in the cap after the cap has been pulled over the end of the needle. In accordance with the invention, this means is in the form of a torsion spring that is disposed in the cap. The spring is in the form of a coil with two outstanding legs and is bottom in the bottom of the cap. When in place, one leg of the spring is biased against the needle with the cap in place on the housing. When the cap has been extended over the end of the needle, this legs snaps over the bore in the cap against an opposed inner wall of the cap thereby blocking a return movement of the needle through the bore.

In accordance with the invention, the hollow Huber needle is a straight needle with a bent distal end that is secured in the housing. In addition, the housing has a bore extending perpendicularly of the needle for receiving a flexible line and a chamber communicating this bore with a proximal end of the needle for transferring liquids therebetween.

The flexible line that serves to deliver a medicament or the like to the internal chamber of the housing and, thus, to the Huber needle is secured within the bore. One advantage of this mounting arrangement is that any excess pressure that is delivered through the flexible line, causes the line to expand radially against the internal wall of the bore thereby further securing the flexible line in place against leakage.

These and other objects and advantages of the invention will become more apparent from the following detailed description taken in conjunction with the accompanying drawings wherein:

FIG. 1 illustrates a view of a Huber needle assembly constructed in accordance with the invention;

FIG. 2 illustrates an exploded view of the Huber needle assembly of FIG. 1;

FIG. 6 illustrates a view of the torsion spring relative to the Huber needle during use; and FIG. 7 illustrates a view of a torsion spring with the Huber needle in a retracted position in accordance with the invention.

Referring to FIG. 1, the Huber needle assembly 10 is connected to a line 11 for supplying fluid to a vascular access device (not shown) that is typically implanted under the skin of a patient. As indicated, the line 11 is provided with a pinch clamp 12 in order to control the fluid passing through the line 11 into the Huber needle assembly 10.

Figure 3:
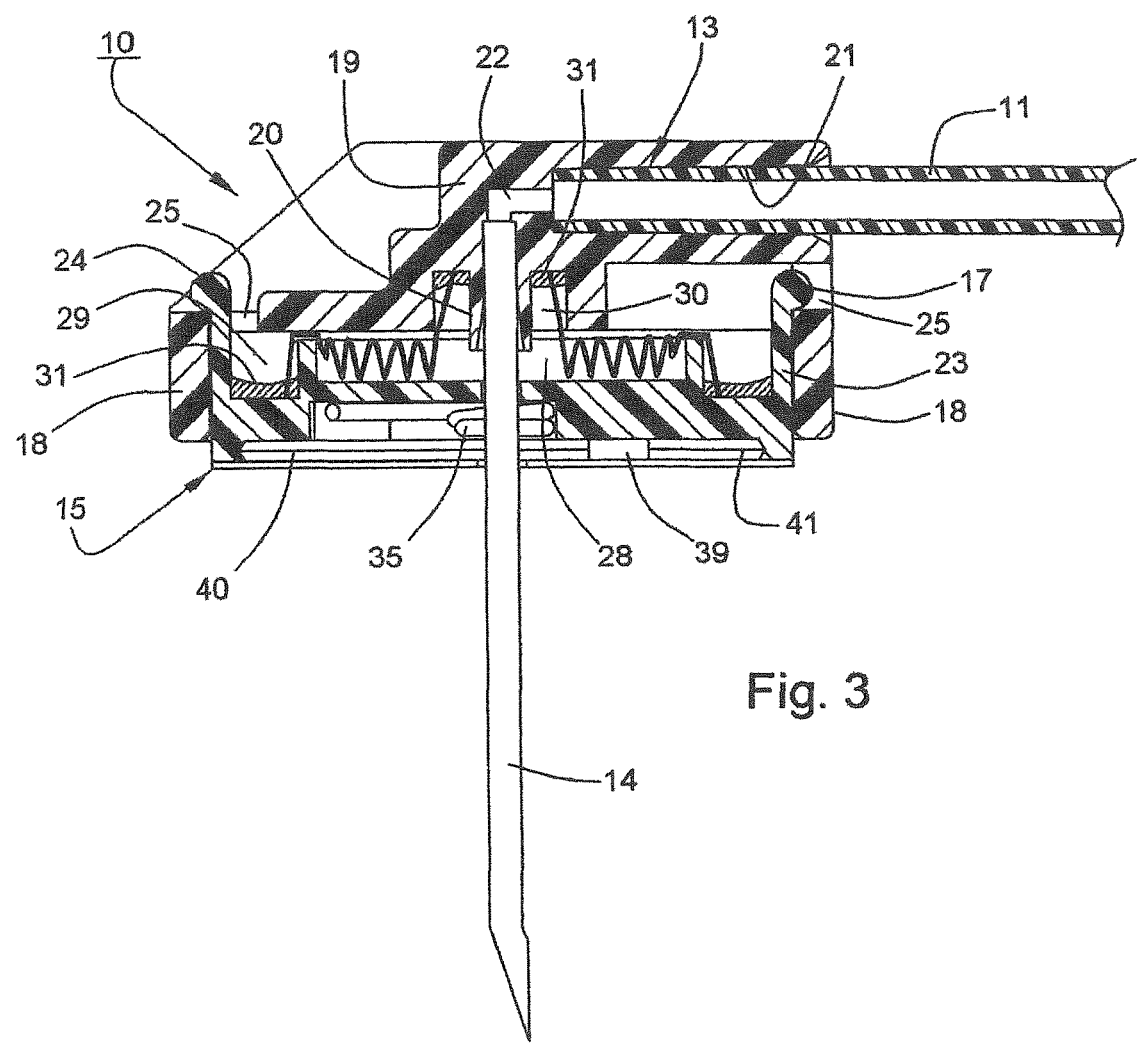
FIG. 3 illustrates a cross-sectional view of the Huber needle assembly of FIG. 1.

Referring to FIGS. 2 and 3, the Huber needle assembly 10 includes a molded one-piece housing 13 in which a straight hollow Huber needle 14 is secured and a molded one-piece cap 15 that is snap fitted into the housing 13 and that can be manually removed from the housing 13.

In addition, the assembly 10 has a sheath or securement bag 16 secured to and between the housing 13 and the cap 15 concentrically of the needle 14 for tethering the cap 15 to the housing 13 when removed therefrom and for encasing the needle 14.

Referring to FIG. 3, the housing 13 is made of any suitable material, such as plastic, and includes a base 17 with depending legs 18 for receiving the cap 15 and an upstanding central portion 19 that provides a manual gripping surface. The upstanding portion 19 has a depending central hub 20 in which the proximal end of the hollow needle 14 is secured in any suitable fashion, for example by use of an adhesive. The upstanding portion 19 also includes a bore 21 that receives the line 11 and an L-shaped internal chamber 22 that communicates at one end with the bore 21 and at the opposite end with the proximal end of the hollow needle 14 for transferring liquids therebetween.

The Huber needle 14 is a hollow straight needle with a bent distal end (see FIG. 3) that is secured in the housing 13 separately from the line 11.

Figure 4:
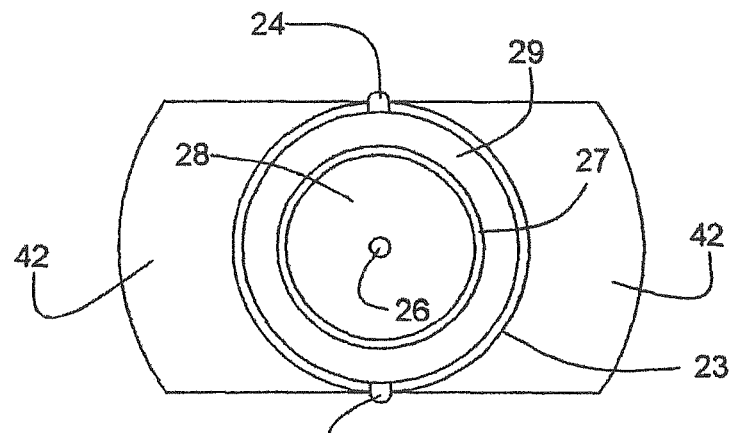
FIG. 4 illustrates a top view of the cap in accordance with the invention.

Referring to FIGS. 3 and 4, the cap 15 is made of any suitable material, such as plastic, and has an upstanding portion 23 of circular shape for fitting into the housing 13 between the depending legs 18. As illustrated, the circular portion 23 has a pair of diametrically opposed rounded projections 24 that pass through openings 25 in the housing 13 to engage over the legs 18 in a snap-fit relation to releasably hold the cap 15 in the housing 13.

The cap 15 also has a central bore 26 for passage of the needle 14 and an upstanding circular wall 27 concentric to the bore 26 to define a circular cavity 28 and coplanar with the circular portion 23 to define an annular recess 29.

Referring to FIGS. 2 and 3, the sheath 16 is of frusto-conical shape with an upper smaller diameter end, as viewed, secured to the housing 13 and a lower larger diameter end secured to the cap 15 in order to tether the cap 15 to the housing 13 when in a separated condition as described below.

As shown in FIG. 3, the upper end of the sheath 16 is secured in an annular recess 30 about the hub 20 of the housing 13 by means of an adhesive 31.

The lower end of the sheath 16 is secured in the annular recess 29 of the cap 15 by a similar adhesive 31.

As indicated in FIG. 2, the sheath 16 is of conical shape when extended. When collapsed, the sheath 16 fills the central cavity 28 of the cap 15 with the smaller end of the sheath collapsed within the larger end of the sheath. By forming the sheath 16 in a conical manner, the collapsed state of the sheath 16 is better received within the central cavity 28 of the cap 15 than if the sheath were a tubular sheath.

The sheath 16 is constructed as described in published US Application No. US2003/0114797, that is, the sheath 16 is characterized in having a high tensile strength that allows the sheath 16 to be pulled out from the collapsed condition of FIG. 3 to an extended state without breaking. The sheath 16 is made of two strips of film material and preferably of a polyester, such as Mylar, that are heat sealed together along two longitudinal edges using a co-extruded heat-sealable backing of a polyethylene, such as Surlyn. The construction of the sheath is such that the sheath can be longitudinally collapsed to a significantly greater degree than if the sheath were made as an extruded tube of polyester.

The sheath 16 is made of a transparent material to permit viewing of the needle 14.

Figure 5:
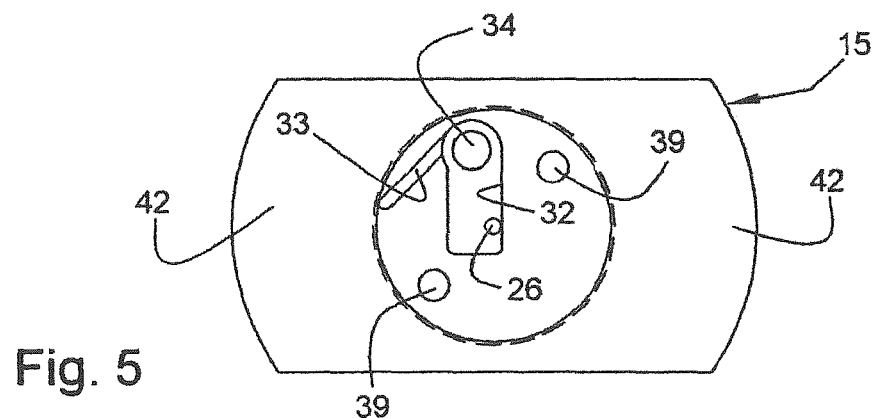
FIG. 5 illustrates a bottom view of the cap in accordance with the invention.

Referring to FIG. 5, the cap 15 is also provided with a recessed compartment 32 of generally rectangular shape in the bottom surface and a smaller recess 33 that extends angularly of the compartment 32. The compartment 32 contains an integral post 34 near one end and the bore 26 of the cap 13 passes through the compartment 32.

A means 35 is provided in the cap 15 for closing over the bore 26. As shown in FIG. 6, this means 35 is in the form of a torsion spring that has a coil 36 disposed over the post 34 and two outstanding legs 37, 38. One leg 37 of the spring 35 is disposed in the recess 33 in the bottom of the cap 15 in a tight-fit manner and the other leg 38 is disposed in the compartment 32 to engage the needle 14 passing through the bore 26. In addition, as indicated in FIG. 7, this leg 38 has a folded over end of a size, i.e. a width, greater than the size, i.e. the diameter, of the bore 26 in the cap 15.

As shown in FIG. 5, the cavity 28 of the cap 15 has a pair of diametrically positioned posts 39.

Referring to FIGS. 2 and 3, a spring retainer 40 is secured within a circular recess 41 in the bottom of the cap 15 to retain the spring 35 in place. The retainer 40 may be of any suitable material, such as plastic or metal, and may be secured within the recess 41 of the cap 15 in any suitable manner, such as by a suitable adhesive. As indicated in FIG. 3, the retainer 40 has a central aperture for passage of the Huber needle 14 and has a pair of apertures receiving the two posts 39 in the cap 15. During assembly, a suitable adhesive is applied to the posts 39 to secure the retainer 40 in place.

As indicated in FIGS. 4 and 5, the cap 15 is provided with an integral pair of wings 42 of conventional structure that extend laterally from the cap 15 to facilitate mounting of the Huber needle assembly 10 against the skin of a patient.

A foam pad 43 is also disposed over the bottom of the cap 15, i.e. over the retainer 23 and wings 42 in order to provide a soft surface that can be placed against the skin of a patient.

Referring to FIG. 1, the Huber needle assembly 10 is provided with a tubular sheath 44 that is placed over the exposed end of the Huber needle 14 prior to use.

In order to use the Huber needle assembly 10, the tubular sheath 44 is removed in order to expose the Huber needle 14. The needle assembly 10 can then be inserted into a vascular access device implanted within a patient in a conventional manner.

In order to remove the Huber needle assembly 10 from a patient, the user applies pressure against the two wings 42 extending from the cap 15 in order to hold the cap 15 in place while using a second hand to grip the upstanding portion 19 and lifting the housing 13 away from the cap 15.

When the housing 13 is pulled from the cap 15, the two projections 24 on the cap 15 are able to flex radially inwardly allowing the housing 13 to disengage from the cap 15.

As the housing 13 moves away from the cap 15, the sheath 16 is played out from its collapsed state into the extended state indicated in FIG. 2. Also, during this time, the movable leg 38 of the torsion spring 35 remains engaged with the needle 14. However, as the needle 14 emerges from the vascular access device and passes through the compartment 31 into the bore 26 in the cap 15, the movable leg 38 of the torsion spring 35 snaps across the bore 26 and against an internal wall of the compartment 31 thereby blocking any return movement of the needle 14 through the bore 26.

The tension in the torsion spring 35 is such that when the movable leg 38 of the torsion spring 35 snaps over the opening 26, there is a significant click or sound that can be heard by the user as an indication that the needle 14 has been fully retracted.

When the Huber needle 14 has been fully retracted, the sheath 16 is in a slightly stretched condition so as to bias the housing 13 and cap 15 towards each other. This results in the distal end of the Huber needle 14 abutting the movable leg 38 of the torsion spring 35 under a slight pressure so that the cap 15 does not hang loose but instead holds the distal end of the needle 14 in a closed manner.

Since the cap 15 is closed, the end of the needle 14 is maintained in a sealed manner. As this time, the Huber needle assembly 10 may be discarded with the needle 14 contained in a protective manner.

The invention thus provides an improved Huber needle assembly that provides for the automatic sheathing of the distal end of a Huber needle during removal from a vascular access device.

Further, the invention allows the Huber needle assembly to transfer fluids under high pressure, for example, under 300 psi during an emergency procedure.

What is claimed is:

1. A safety needle assembly comprising:
   a cap;
   a housing movable relative to the cap from a first position adjacent the cap to an extended second position spaced from the cap;
   a hollow needle having a proximal end and a distal end extending along a common axis, the proximal end secured in and extending from the housing;
   a line for supplying a fluid to the safety needle assembly extending perpendicular to the axis; and
   a continuous film sheath concentrically disposed about the needle in a collapsed state with the housing in the first position, the sheath secured to both the cap and the housing, the sheath extendable from the collapsed state to an extended state in response to movement of the housing from the first position to the second position, the sheath having a frusto-conical shape.

2. The safety needle assembly according to claim 1, further comprising a needle safety component disposed in a first cavity that translates from an engagement position, wherein a portion of the component is engaged with the needle when the housing is in the first position, to a safety position, wherein the portion covers an opening in a bottom surface of the cap when the housing is in the second position.

3. The safety needle assembly according to claim 2, wherein the cap comprises a second cavity separated from the first cavity, the needle safety component disposed in the first cavity and the sheath disposed in the collapsed state in the second cavity when the housing is in the first position.

4. The safety needle assembly according to claim 1, wherein the housing has a bore extending perpendicularly of the needle for receiving the line therein and a chamber communicating the bore with a proximal end of the needle for transferring a liquid delivered at high pressure from the line into the needle.

5. The safety needle assembly according to claim 1, wherein the cap comprises a circular portion including a pair of diametrically opposed projections, and the housing comprises openings that receive the projections in the first position to releasably hold the housing in the cap.

6. The safety needle assembly according to claim 5, wherein the cap comprises an upstanding circular wall defining a second cavity coplanar with the circular portion, the circular wall and circular portion together defining an annular recess.

7. The safety needle assembly according to claim 1, wherein the cap comprises an integral pair of laterally extending wings.

8. The safety needle assembly according to claim 1, further comprising a foam pad disposed on a bottom surface of the cap.

* * * * *